United States Patent
Wilhelm

(10) Patent No.: US 9,518,913 B2
(45) Date of Patent: Dec. 13, 2016

(54) METHOD FOR DETECTING PARTICLES IN A FLUID STREAM

(71) Applicant: Hydac Filter Systems GmbH, Sulzbach/Saar (DE)

(72) Inventor: Andreas Wilhelm, Dillingen (DE)

(73) Assignee: HYDAC FILTER SYSTEMS GMBH, Sulzbach/Saar (DE)

( * ) Notice: Subject to any disclaimer, the term of this patent is extended or adjusted under 35 U.S.C. 154(b) by 48 days.

(21) Appl. No.: 14/403,751

(22) PCT Filed: Jun. 20, 2013

(86) PCT No.: PCT/EP2013/001822
§ 371 (c)(1),
(2) Date: Nov. 25, 2014

(87) PCT Pub. No.: WO2014/005673
PCT Pub. Date: Jan. 9, 2014

(65) Prior Publication Data
US 2015/0121994 A1 May 7, 2015

(30) Foreign Application Priority Data
Jul. 3, 2012 (DE) .......................... 10 2012 013 255

(51) Int. Cl.
*G01N 15/10* (2006.01)
(52) U.S. Cl.
CPC .......... *G01N 15/10* (2013.01); *G01N 15/1031* (2013.01); *G01N 2015/1068* (2013.01)

(58) Field of Classification Search
CPC ................ G01N 15/10; G01N 15/1031; G01N 2015/1068
See application file for complete search history.

(56) References Cited

U.S. PATENT DOCUMENTS

2011/0170659 A1* 7/2011 Ohzu ................... G01N 23/223
378/50

FOREIGN PATENT DOCUMENTS

| DE | 689 17 480 T2 | 12/1994 |
|---|---|---|
| DE | 10 2006 018 964 A1 | 10/2007 |
| DE | 10 2007 052 047 A1 | 5/2009 |
| DE | 10 2010 040 717 A1 | 4/2012 |
| EP | 0 766 086 A2 | 4/1997 |
| GB | 2 004 374 A | 3/1979 |

* cited by examiner

*Primary Examiner* — Paul West
(74) *Attorney, Agent, or Firm* — Wenderoth, Lind & Ponack, L.L.P.

(57) ABSTRACT

A method for detecting particles in a fluid stream includes generating a measurement field that can be passed through by the fluid stream, acquiring and evaluating measurement values of the fluid stream passing through the measurement field, and detecting at least one particle by way of a distinctive sequence of measurement values. Each of the distinctive successions of measurement values is acquired and evaluated to determine if a particle or a gas bubble is passing through the measurement field.

17 Claims, 6 Drawing Sheets

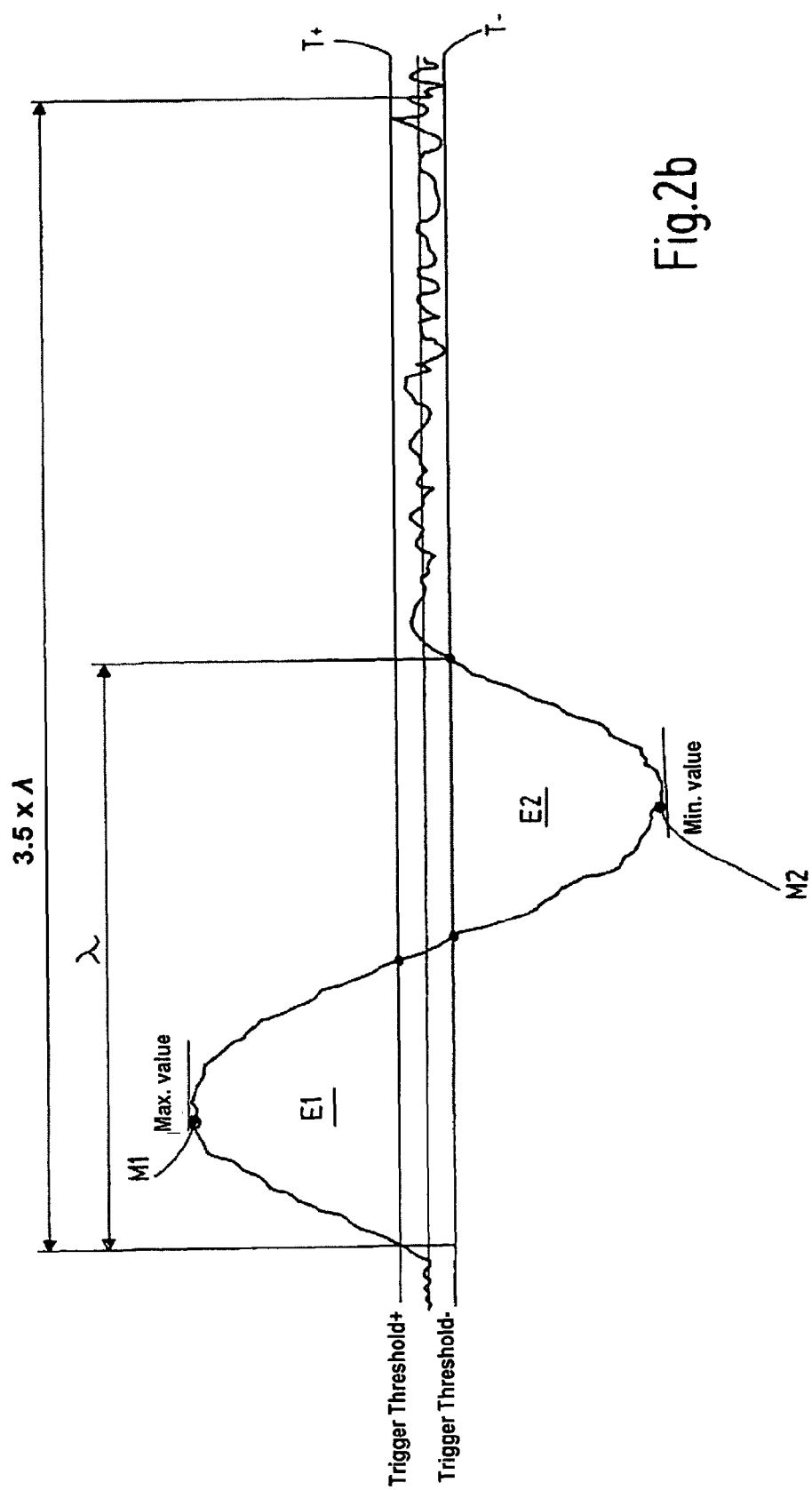

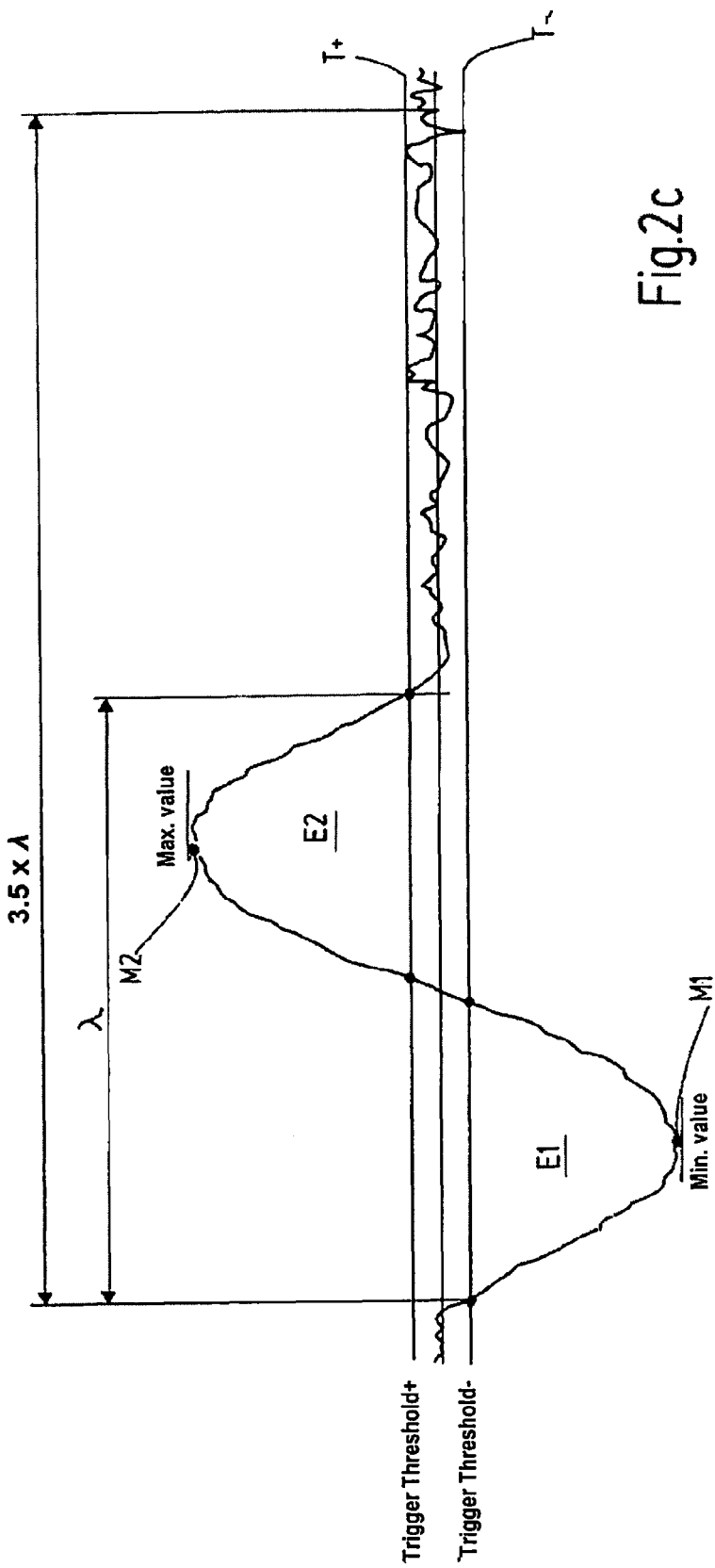

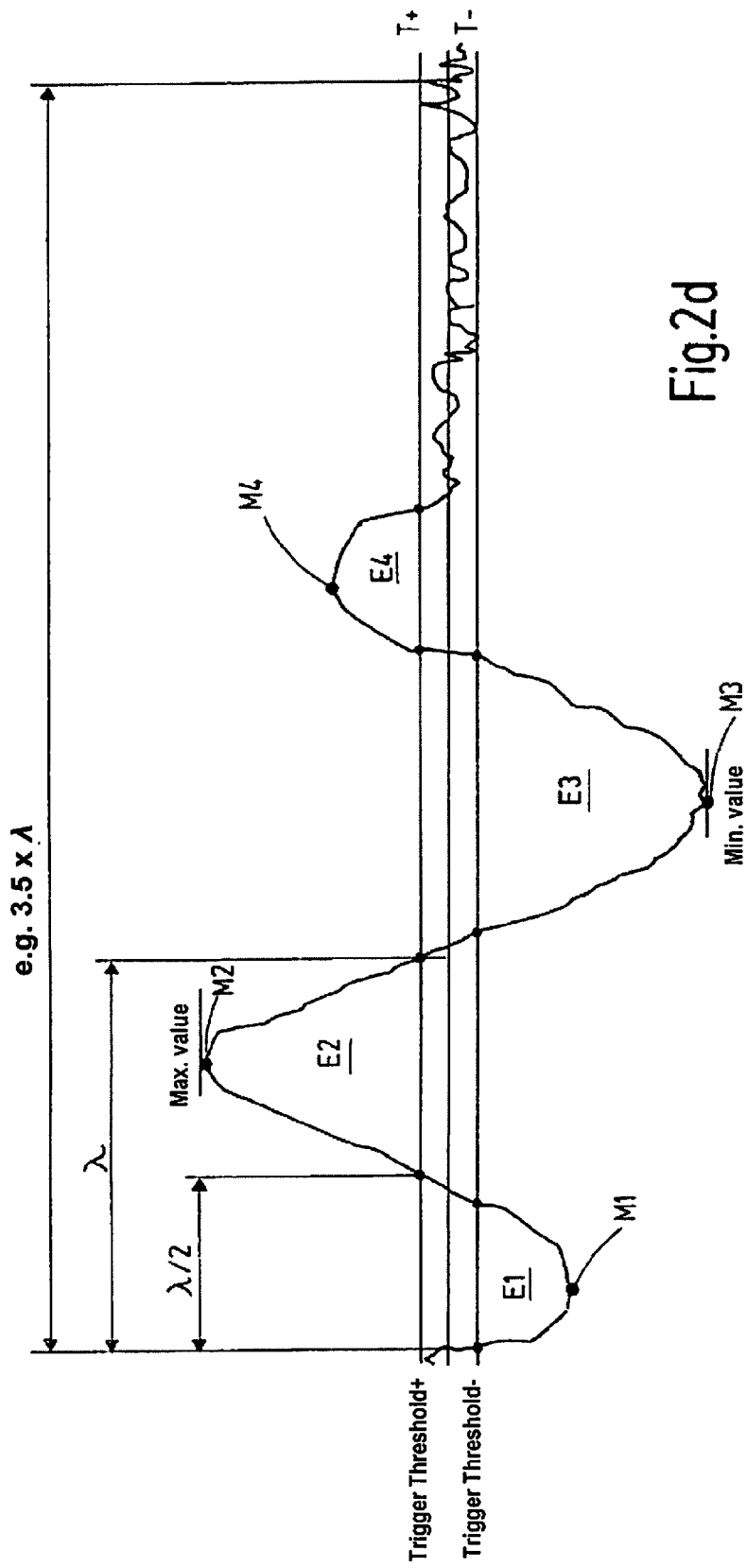

METHOD FOR DETECTING PARTICLES IN A FLUID STREAM

FIELD OF THE INVENTION

The invention relates to a method for detecting particles in a fluid stream, comprising generating a measurement field that can be passed through by the fluid stream, recording and evaluating of measurement values of the fluid stream passing through the measurement field, and detecting at least one particle, in each case by a characteristic sequence of measurement valves.

BACKGROUND OF THE INVENTION

Such a method is known, for example, from WO 2007/088015 A1. In the known method, a magnetic field covering at least sections of the fluid stream is generated by at least one field coil, and, via two sensor coils, each of which may be connected to an evaluation device. The presence of a particle in the fluid stream is detected from the signal induced in the respective sensor coil. If a particle flows through the section or the magnetic field covered by the field coil, the voltage induced in the respective sensor coil changes in such a way that a detection signal may be tapped and evaluated via the evaluation unit. In the known method, two sensor coils wound in opposite directions are used. As a result of those two sensor coils the sensitivity with respect to the particle to be detected is increased. For example, smaller particles having a size of 50 to 100 micrometers may also be detected.

By such methods, particles are detected in the fluid or fluid stream in a system for cooling and/or for lubricating components of a drive unit with the aid of a fluid, in particular for cooling and/or for lubricating a gear unit of a wind turbine. Maintenance of such systems in wind turbines is particularly costly due to the high mounting location of the gear unit. Detecting at an early stage particle loads caused by wear of mechanical components or by dirt entering from the outside that may particularly damage to the cooling system and/or lubricating system is therefore desirable. In addition to the particles, gas bubbles, in particular air bubbles, are sometimes also detected as particles, to be trapped in the fluid guided through the respective system. Because of the false positive identification of air bubbles as particles, early damage detection is adversely affected, since an actual rise in the particle count rate may only occur beyond the signal noise to be associated with the air bubble signals. Consequently, an excessively high particle load is sometimes indicated and potential damage is indicated prematurely.

SUMMARY OF THE INVENTION

An object of the invention is to provide an improved method for detecting particles in a fluid stream, which enables the actual particle load of the fluid in a fluid stream to be reliably determined.

This object is basically achieved by a method where the characteristic sequence of measurement values is recorded and evaluated in each case in terms of whether a particle or a gas bubble is passing through the measurement field.

Typically, air bubbles are detected as gas bubbles. The gas bubbles or air bubbles may appear due to foam in gear units, which are lubricated with the aid of the fluid in the fluid stream. The gear unit is, in particular, a wind turbine gear unit, which is difficult to access at its high mounting location. According to the invention, a gas bubble detection takes place to the extent that a gas bubble as such is detected and is differentiated from a particle. The relevant particle load, in other words, particle contamination, includes exclusively the actual particles present in the fluid or fluid stream.

The method according to the invention may be used to measure and monitor the load or contamination of a fluid stream with particles. However, measuring and monitoring the load of a fluid stream with gas bubbles can be done, for example, to determine an associated foam formation. The method according to the invention is not limited in use to fluids or fluid streams in a system for cooling and/or lubricating components of a drive unit, such as a gear unit. Additional applications in the manufacturing, in the transport and in the processing of fluids of any type are possible.

In one preferred variant of the method according to the invention, the measurement values are each recorded and evaluated for an observation period, which period is greater than the measurement duration for a sequence of measurement values characteristic of a particle and/or a gas bubble. This variant of the method is appropriate, in particular if the sequence of measurement values characteristic of a particle has a measurement duration that differs from that of a sequence of measurement values characteristic of a gas bubble. As soon as a particle or gas bubble is detected by the associated characteristic sequence of measurement values, it is verified whether the measured sequence is in fact characteristic of a particle or of a gas bubble by observing the further curve of the measurement values beyond the respective measurement duration. Preferably, the observation period is at least double, preferably 3.5 times the corresponding measurement duration.

The sequence of measurement values characteristic of a particle typically has a signal shape. Another sequence of measurement values characteristic of a gas bubble has another signal shape. Furthermore, the signal shape for a particle and the other signal shape for a gas bubble may at least partially coincide, in other words, follow, at least in sections, the same curve. In this preferred variant, the method according to the invention may be very efficient, i.e., may be carried out with minimal expenditure of time or measurement effort, since initially the particle characterized by the shorter signal, a particle or a bubble, is detected, and with an immediately following measurement, a determination is made whether in fact this particle or the particle characterized by a longer signal shape, a gas bubble or a particle, is present in the fluid stream.

For example, the signal shape for a particle may have at least one extremum, preferably two extrema, and/or follow a periodic curve, preferably a sinusoidal curve. The other signal shape for a gas bubble may also have at least three extrema, preferably four extrema and/or follow a periodic curve, preferably a sinusoidal curve. Each extremum is expediently identified and evaluated by the exceeding of and the subsequent dropping below an upper limit value or by the dropping below and the subsequent exceeding of a lower limit value of the recorded measurement values. In the case of signal shapes for the particle and the gas bubble having a different number of extremum values or extrema, with the number of consecutively measured extrema, whether a particle or a gas bubble is present in the fluid stream can be determined.

To avoid a falsification of the measurement result caused by a noise of the measurement values, such noise is taken into consideration in a preferred variant of the invention in such a way that only measurement values outside a predefined noise band between a lower noise value and an upper noise value are taken into consideration.

Additional advantages and features of the invention are apparent from the figures and the following description of the drawings. The aforementioned features and those cited below may, according to the invention, be implemented alone or in arbitrary combinations in conjunction with the method according to the invention.

Other objects, advantages and salient features of the present invention will become apparent from the following detailed description, which, taken in conjunction with the drawings, discloses a preferred embodiment of the present invention.

BRIEF DESCRIPTION OF THE DRAWINGS

Referring to the drawings that form a part of this disclosure and that are purely schematic and are not to scale:

FIGS. 2a-2d show curves of measurement values recorded and evaluated for a defined observation period, taking into account a noise band, lower and upper limit values, a sequence of measurement values characteristic of a particle and/or another sequence of measurement values characteristic of a gas bubble.

DETAILED DESCRIPTION OF THE INVENTION

Figure 1A:
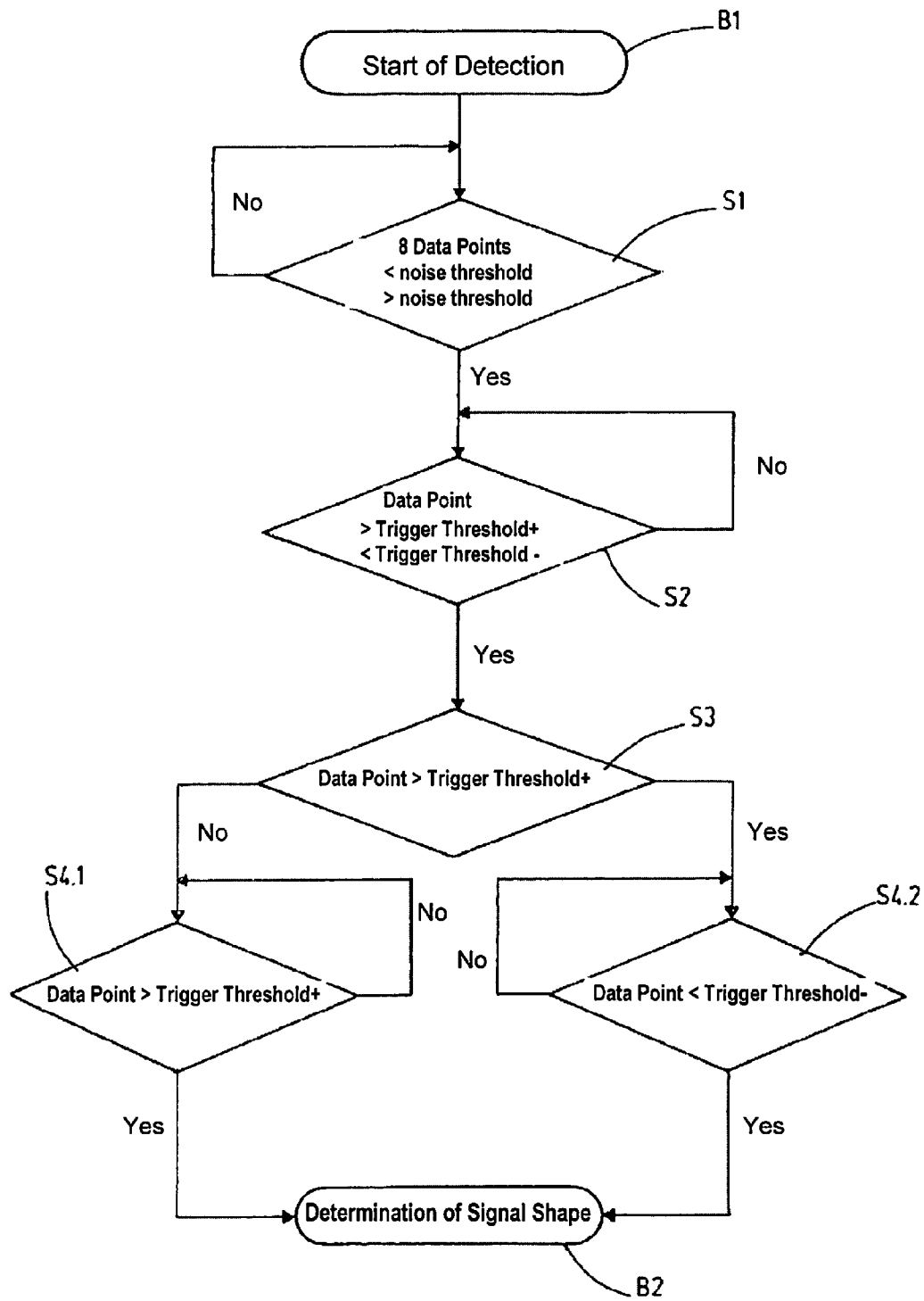
FIGS. 1a and 1b are a flow chart of a method according to an exemplary embodiment of the invention.
Figure 2A:
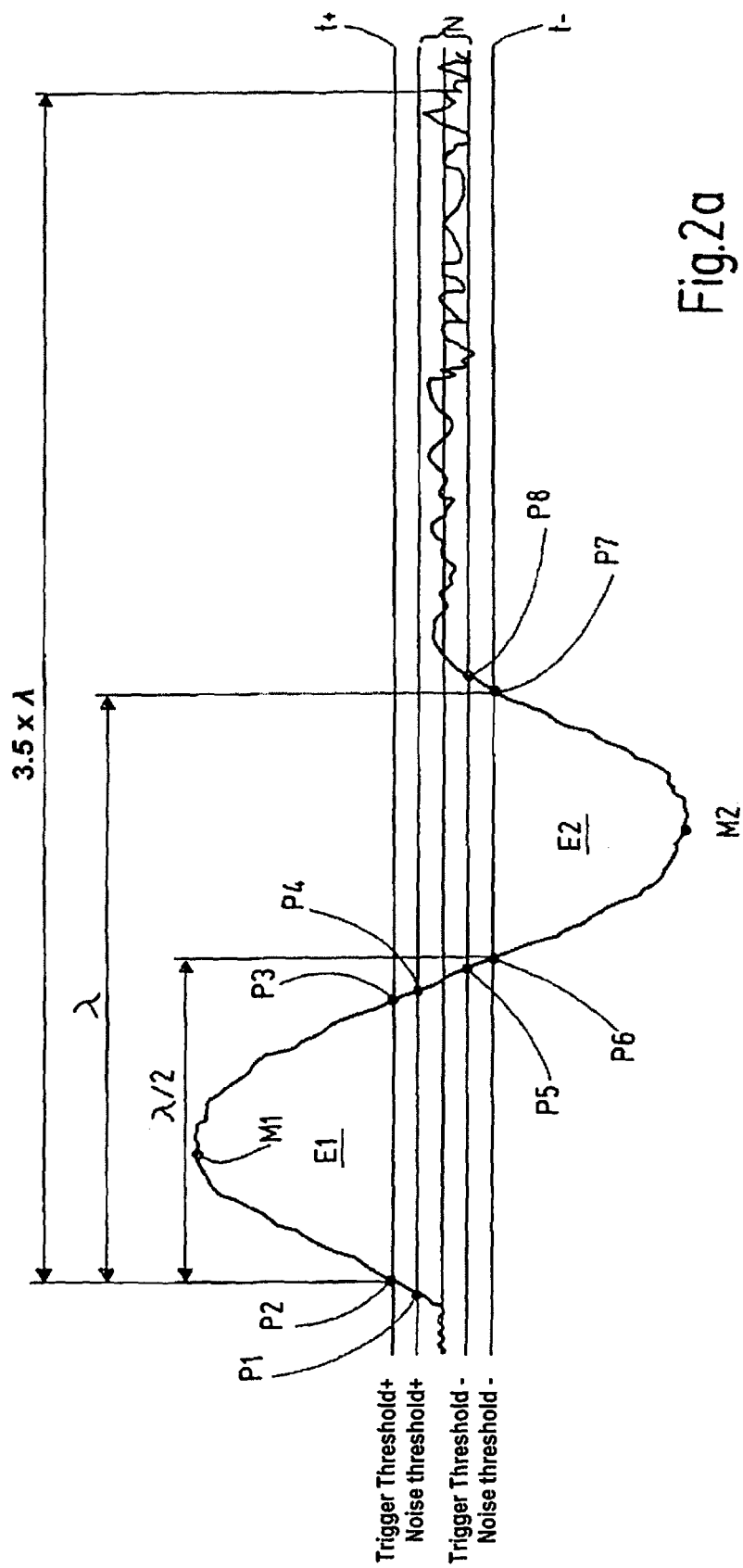

FIG. 1a shows the steps of the method according to the invention from the first start B1 of the registering of a characteristic sequence of measurement values to the second start B2 of the identification or verification of whether a particle or a gas bubble has been detected. In the first step S1, it is verified whether eight measurement values or data points lie within a noise band. The noise band is defined by an upper noise value, noise level+, and a lower noise value, noise level−. In the exemplary embodiment shown, a particle is characterized by a signal shape having two consecutive extrema E1, E2, and a gas bubble is characterized by another signal shape having four consecutive extrema E1-E4. FIGS. 2a through 2c each show the signal shape for a particle. FIG. 2d shows the other signal shape for a gas bubble. A pause between two consecutive signal shapes characteristic of a particle or a gas bubble, in other words, a pause between two signals, is identified via at least eight measurement values or data points within the noise band N. As long as at least eight data points do not lie within the noise band N, it is possible, for example, that a preceding sequence of measurement values, or a signal sequence characteristic of a particle or gas bubble, for example, is not yet completed. A characteristic signal shape, in other words, a signal, includes far more than eight measurement values or data points P1-P8.

In the second step S2, it is queried whether the data points or measurement values exceed an upper trigger level t+ or drop below a trigger level t−. The upper trigger level t+ and the lower trigger level t− represent inasmuch an upper limit level and a lower limit level. In the curve of the measurement values, or the measurement signals, shown in FIG. 2a, the measurement values lying between the data points P2 and P3 and the measurement values lying between the data points P6 and P7 meet this condition.

In the third step S3, it is evaluated, whether a maximum having measurement values above the upper trigger level t+ or a minimum having measurement values below the lower trigger level t− is present. FIG. 2a shows a measurement signal having a maximum value M1 as the first extremum E1 between the data points P2 and P3, as well as a minimum value M2 as the second extremum E2 between the data points P6 and P7.

In the fourth step S4.1 for a minimum and S4.2 for a maximum, the length λ/2 of the first half-wave is determined. In the exemplary embodiment shown, the signal shapes characteristic of a particle or a gas bubble are formed, following a sinusoidal curve, in such a way that the wave length λ of a sine wave characteristic of a particle having two extrema E1, E2 corresponds to the measurement duration of this characteristic sequence of measurement values. The beginning of the first half-wave is defined in conjunction with the exceeding of or the dropping below the respectively associated trigger level t+, t−, and the end of the first half-wave by the dropping below or exceeding of the respective, opposite trigger level t−, t+. As soon as the respective opposite trigger level t+, t− is fallen short of or exceeded, in other words, broken through, the condition for the signal trigger is met and the entire wave length λ of the sine wave or sine curve is calculated from the length λ/2 of the first half-wave.

For the subsequent determination of the measured signal shape beginning at the second start B2 and, corresponding to the detected particle, of a particle or a gas bubble, the wave length λ, preferably 3.5 times that of the wave length λ, is stored in an analysis buffer. The observation period to be subsequently evaluated begins with the first exceeding or falling below of the associated trigger level t+, t−, in FIG. 2a at data point P2, and ends after 3.5 times the wavelength λ at the aforementioned time or data point P2. The representations of FIGS. 2b-2d differ from the representation of FIG. 2a in that in the former, in each case, no noise band is delineated.

Figure 1B:
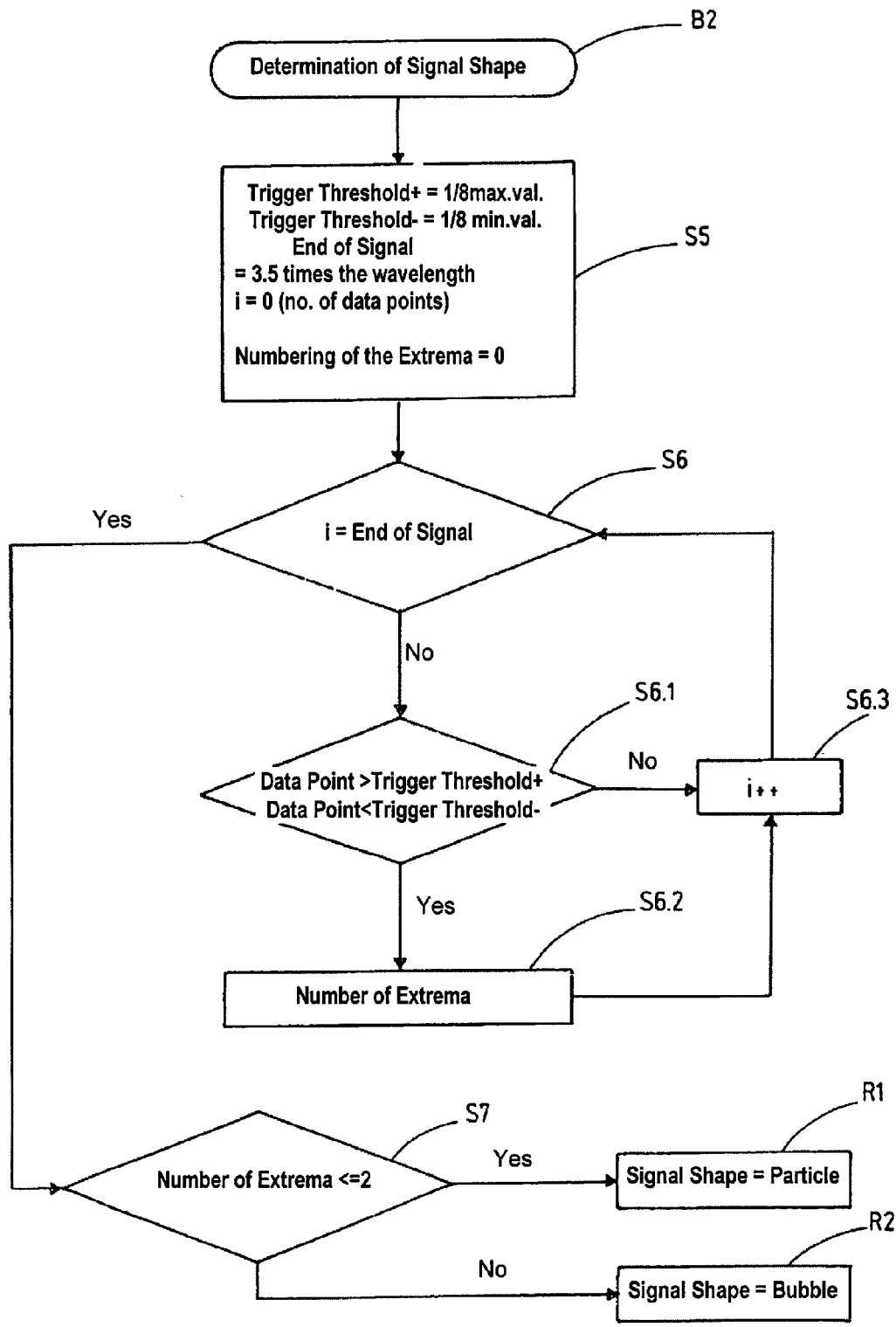

FIG. 1b shows the steps according to the method of the present invention of determining the signal shape from the second start B2 to two alternative results, result R1 for a particle, or result R2 for a gas bubble. In the fifth step S5, an upper limit value T+ and a lower limit value T− are calculated from the amplitudes of the measured sine waves, in other words, from the extremum values M1, M2 of both extrema E1, E2. In the exemplary embodiment shown, each limit value T+, T− is, in each case, ⅛ of the associated extreme value M1, M2. Partial ratios deviating from the former may be selected. If, comparable to the representation in FIG. 2d, two or more maxima E2, E4 and/or two or more minima E1, E3 are present, the global maximum and the global minimum, in FIG. 2d, the second extremum E2 formed as the maximum and the third extremum E2 formed as the minimum, are used for determining the upper limit value T+ and the lower limit value T−, respectively.

Furthermore, the length of the observation period is set at 3.5 times the wavelength A, wherein multiples deviating therefrom, for example, two-fold, are conceivable. The numbering of the data points or measurement values and the numbering of the extrema are each reset to 0. The now evaluated and analyzed observation period begins with the first exceeding of or dropping below the associated limit value T+, T−, and ends after 3.5 times the wavelength λ as of the aforementioned data point or measurement value. In addition to the wavelength λ, at least one data point or measurement value, expediently, the respective extreme value M1-M4, is stored in a cache or analysis buffer for each extremum E1-E4.

The data points or extreme values M1-M4 stored in the cache or analysis buffer are verified in the sixth step S6 with respect to the number of extrema E1-E4 or extreme points present. Based on the first extreme value M1, which lies above the upper limit value T+ or below the lower limit value T−, the number 1 of the extrema E1-E4 when exceeding or dropping below the respective, opposite limit value T−, T+, is incremented in each case, i.e., increased by 1.

Once the measurement values pass through the observation period and are analyzed in the process, in the seventh step S7, whether a maximum of two or more extreme points have been counted is determined. Two extreme points E1, E2 corresponding to the representations in FIGS. 2b and 2c indicate, in accordance with the signal type or the characteristic signal shape, a particle as result 1 R1. Four extrema E1-E4 indicate, in accordance with the representation of FIG. 2d, the other signal shape characteristic of a gas bubble, and lead to result R2.

The representations of FIGS. 2b and 2d differ in that in FIG. 2b a global minimum E2 follows a global maximum E1, and in FIG. 2c a global maximum E2 follows a global minimum E1. FIG. 2d shows a succession of a local minimum E1, a global maximum E2, a global minimum E3 and a local maximum E4. Crucial for the detection of a gas bubble is the number of more than two extreme points E1-E4. Thus, all extrema E1-E4 may have the same amplitude, in other words, identical extreme values M1-M4 in terms of amount. Furthermore, the signal measured in the observation period may, in departing from a sinusoidal curve, be a square wave signal, a triangle signal or the like.

The local extrema, the local minimum E1 as first extremum and the local maximum M4 as fourth extremum shown in FIG. 2d represent a type of back and forth oscillation for a succession of two global extrema, the global maximum E2 and the global minimum E3, which are characteristic of a particle. In the situation in FIG. 2d, the length $\lambda/2$ of the half-wave is determined and, accordingly, the wavelength $\lambda$ is calculated, and the length of the observation period is defined by the beginning of the minimum E1 as first extremum, as well as the subsequent exceeding of the upper limit value T+.

While one embodiment has been chosen to illustrate the invention, it will be understood by those skilled in the art that various changes and modifications can be made therein without departing from the scope of the invention as defined in the claims.

The invention claimed is:

1. A method for detecting particles in a fluid stream, comprising:
   generating a measurement field;
   passing the measuring field through the fluid stream;
   recording and evaluating measurement values in the fluid stream from the measurement field;
   detecting a particle by a characteristic sequence of the measurement values;
   recording and evaluating the characteristic sequence of the measurement values in terms of whether a particle or gas bubble is passing through the measurement field for an observation period greater than a measurement duration of a sequence of the measurement values characteristic of at least one particle or of at least one gas bubble; and
   determining whether a maximum of two or more extreme points have been counted once measurement values pass through the observation period.

2. A method according to claim 1 wherein the observation period is at least double the measurement duration.

3. A method according to claim 1 wherein the observation period is 3.5 times the measurement duration.

4. A method according to claim 1 wherein
the sequence of the measurement values that is characteristic of a particle has a particle signal shape; and
the sequence of the measurement values that is characteristic of a gas bubble has a gas bubble signal shape, the particle signal shape and the gas bubble signal shape being different.

5. A method according to claim 4 wherein the particle signal shape and the gas bubble signal shape at least partially coincide.

6. A method according to claim 4 wherein the particle signal shape has at least one extremum.

7. A method according to claim 6 wherein the particle signal shape has at least two extrema.

8. A method according to claim 6 wherein the particle signal shape follows a periodic curve.

9. A method according to claim 8 wherein the periodic curve is a sinusoidal curve.

10. A method according to claim 6 wherein each extremum is identified and evaluated by exceeding and subsequently dropping below at least one of an upper limit value or a lower limit value of recorded measurement values.

11. A method according to claim 4 wherein the gas bubble signal shape has at least three extrema.

12. A method according to claim 11 wherein the gas bubble signal shape has at least four extrema.

13. A method according to claim 11 wherein the gas bubble signal shape follows a periodic curve.

14. A method according to claim 13 wherein the periodic curve is a sinusoidal curve.

15. A method according to claim 11 wherein each extremum identified and evaluated by exceeding and subsequently dropping below at least one of an upper limit value or a lower limit value of recorded measurement values.

16. A method according to claim 1 wherein a noise of the measurement values is considered in evaluating such that only measurement values outside a predefined noise band between a lower noise value and an upper noise value are considered in the evaluating.

17. A method according to claim 1 wherein air bubbles are detected as gas bubbles.

* * * * *